United States Patent [19]
Vacirca

[11] Patent Number: 4,848,163
[45] Date of Patent: Jul. 18, 1989

[54] EXTENDED RANGE LINEAR FLOW TRANSDUCER

[75] Inventor: Joseph S. Vacirca, Lititz, Pa.

[73] Assignee: Timeter Instrument Corporation, Lancaster, Pa.

[21] Appl. No.: 114,701

[22] Filed: Oct. 30, 1987

[51] Int. Cl.⁴ .............................. G01F 1/40; G01F 1/42
[52] U.S. Cl. ................................. 73/861.52; 73/861.61
[58] Field of Search .............. 73/861.52, 861.42, 861.61

[56] References Cited

U.S. PATENT DOCUMENTS

| | | |
|---|---|---|
| 2,127,501 | 8/1938 | Dall . |
| 2,306,940 | 12/1942 | Fischer . |
| 2,463,473 | 3/1949 | Boothby ........................ 73/861.52 |
| 2,842,962 | 7/1958 | Dall . |
| 2,984,105 | 1/1956 | Nagel . |
| 3,071,001 | 1/1963 | Goldsmith . |
| 3,071,160 | 1/1963 | Weichbrod ..................... 73/861.52 |
| 3,349,619 | 10/1967 | Millar ............................ 73/861.52 |
| 3,504,542 | 4/1970 | Blevins . |
| 3,626,755 | 12/1971 | Rudolph ........................ 73/861.52 |
| 3,680,376 | 8/1972 | Catheron . |
| 3,733,898 | 5/1973 | Yamamoto . |
| 3,952,577 | 4/1976 | Hayes . |
| 4,074,573 | 2/1978 | Nordhofen . |
| 4,130,017 | 12/1978 | Benedict . |
| 4,372,170 | 2/1983 | Dehart . |
| 4,381,668 | 5/1983 | Sato . |
| 4,403,514 | 9/1983 | Osborn . |
| 4,528,847 | 7/1985 | Halmi . |
| 4,557,296 | 12/1985 | Byrne . |
| 4,559,275 | 12/1985 | Matt . |

FOREIGN PATENT DOCUMENTS 1498421 12/1965 Fed. Rep. of Germany ... 73/861.61
1492508 7/1967 France .

OTHER PUBLICATIONS

Pneumotach Bulletin Model 8883.

Primary Examiner—Herbert Goldstein
Attorney, Agent, or Firm—Martin Fruitman

[57] ABSTRACT

An extended range linear flow transduced with simple construction and compact size. The combination of a divergent air flow section and a linear restrictor a short distance from a flow discontinuity yields a flow transducer with linearity over an extended range of flow rates. The simple construction involves only two different size tubes joined by a funnel or step-like section with the linear flow restrictor located in the larger tube section.

11 Claims, 2 Drawing Sheets

EXTENDED RANGE LINEAR FLOW TRANSDUCER

SUMMARY OF THE INVENTION

This invention deals generally with measuring and testing, and more specifically with rate of flow measurement using a restriction to yield a differential pressure.

Gas flow rate transducers have an inherent problem of maintaining a linear response over a wide range of flow rates. Most such transducers use a pressure tap or pilot tube to produce a varying pressure for variations in flow rate, but typically, the rate of pressure variation will vary dramatically for low and high flow rates. In order to overcome this problem, most existing flow transducers are large, complex and expensive. For instance, a typical flow transducer for 0-1000 liters per minute is one to three feet long and has a complex internal construction consisting of multiple small passages formed by many layers of corrugated metal wrapped tightly together. Moreover, such transducers require constant heating when used for pulmonary testing to prevent internal condensation, and they also use pitot tubes for pressure measurement which have small holes that easily clog.

Such transducers are clearly impractical to use for patient pulmonary testing in any environment other than a permanent facility for such testing.

The present invention changes all that. It is a transducer of such simple construction that it is virtually disposable because of its low cost. Moreover, because of its simple construction with no small passages it could also be easily sanitized for reuse.

The linear flow transducer of the preferred embodiment of the present invention is constructed of two simple plastic tubes joined by a divergent section which is funnel shaped. One end of the smaller tubing is used as the flow input and the other end of the transducer, with the larger tubing, has a screen flow restrictor installed across its end. The key to extended range linearity is that the screen flow restrictor must be located within a distance from the end of the small tubing which is no greater than two diameters of the smaller tubing.

This simple criteria makes it possible for the transducer to yield highly linear pressure reading from its pressure tap over a range up to 1000 liters per minute.

The small size and simplicity of the transducer of the present invention along with the elimination of the need for heating the transducer, provides an extended range transducer which can be used in portable applications. Thus, it is now possible to construct extended range portable pulmonary testing equipment which is no larger than a briefcase, therefore making accurate testing of homebound patients a practical reality.

DETAILED DESCRIPTION OF THE INVENTION

Figure 1:
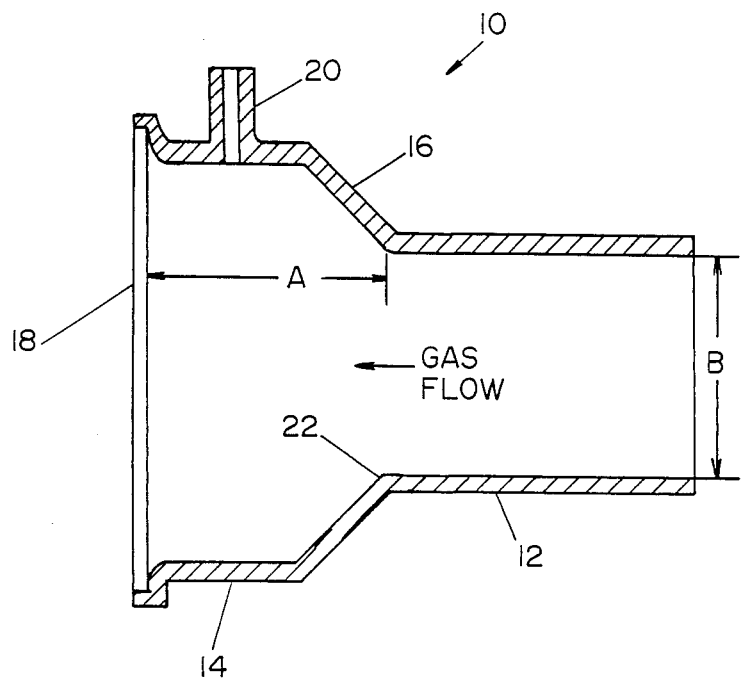
FIG. 1 is an axial cross section view of a preferred embodiment of the invention.

The preferred embodiment of the linear flow transducer of the present invention is shown in FIG. 1 in an axial cross section view. Transducer 10 is essentially constructed of five simple elements: smaller tube 12, larger tube 14, diverging section 16, laminar restrictor 18, and pressure tap 20. The gas flow path is usually into smaller tube 12 and toward flow restrictor 18, but readings are possible in the reverse direction.

The significant structural characteristic of transducer 10 is that laminar restrictor 18, which is typically a small mesh screen, is located within a critical distance from the flow discontinuity caused by internal end 22 of smaller tube 12. This critical dimension shown as A on FIG. 1 must be no more than two times the length of inside diameter B of smaller tube 12.

Apparently, this ratio assures that turbulence created as the gas flow leaves smaller tube 12 is sufficient to have a compensating effect on the pressure monitored by pressure tap 20, so that at higher flow rates, for which pressure normally deviates from the linear relationship to flow, the turbulence counteracts the effects which otherwise would cause the deviation from linearity. The transducer of the present invention therefore maintains the linear relationship between flow and pressure for a greater range of flow rates.

The preferred embodiment of FIG. 1 is constructed by forming entire transducer 10, except for laminar flow restrictor 18, out of plastic, and the length of the preferred embodiment is less than 4½ inches. In the preferred embodiment smaller tube 12 is normally 3.25 inches long and has an inside diameter of 1.0 inch. Divergent section 16 interconnects smaller diameter 12 and larger diameter 14, and is 0.375 inches long. Larger tube 14 is 0.70 inches long and has an inside diameter of 1.75 inches, with the center-line of pressure tap 20 0.35 inches from flow restrictor 18.

In the preferred embodiment, laminar flow restrictor 18 is 500 mesh stainless steel screen with 25% open area. These parameters restrict the gas flow to create sufficient differential pressure from the ambient pressure outside the transducer to be easily mounted by pressure tap 20, and also assure that gas flow through restrictor 18 will remain laminar.

The construction of transducer 10 for the preferred embodiment shown in FIG. 1 locates restrictor screen 18 1.025 inches from the internal end of smaller tube 12, thus yielding a ratio of distance A to internal diameter B of smaller tube 12 of 1.025.

Operational testing of various dimensions of the invention, including models in which dimension A was variable, have established a range of values for the various dimensions and parameters of the preferred embodiment. Smaller tubing 12 should have an inside diameter between ¼ inch and 1½ inches. Larger tubing 14 should have an inside diameter in the range of 1 to 4 inches, and the preferred ratio of the larger tube diameter to the smaller tube diameter is no greater than 4 to 1.

As noted above, the ratio of the distance of the flow restrictor from the internal end of the smaller tube to the diameter of the smaller tube is no more than two to one.

Divergent section 16 should be constructed to have internal surfaces which diverge from the central axis of transducer 10 at angles in the range of 20 to 90 degrees.

Flow restrictor 18 should have an open area of at least 15% and mesh size in the range of 300 to 800 strands per inch.

Transducers built within these limiting ranges of values can be expected to yield essentially linear flow to pressure relationships for flow rates to as high as 1000 liters per minute.

Figure 2:
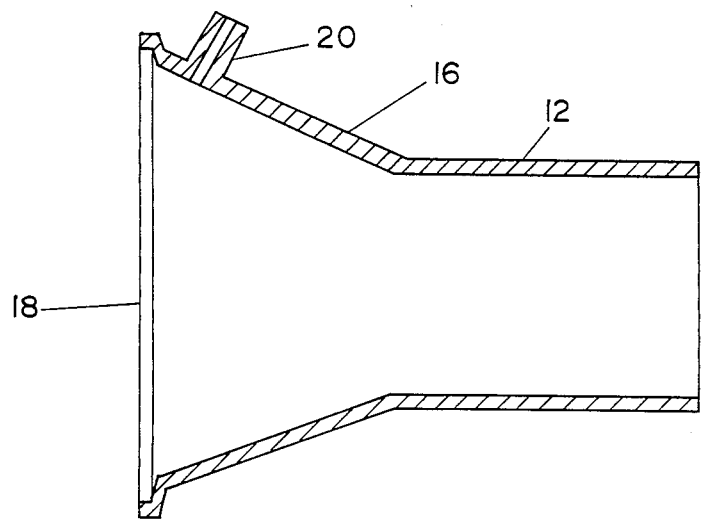
FIG. 2 is an axial cross section view of an alternate embodiment of the invention.

FIG. 2 shows an alternate embodiment of the invention which has an even simpler construction than the embodiment of FIG. 1 in that it eliminates the larger tube section.

Since the larger tube section functions mostly to locate pressure tap 20 and to retain flow restrictor 18, when these functions can be performed by divergent section 16, the larger tube is not required. Thus, in FIG. 2, pressure tap 20 is located on divergent section 16 near flow restrictor 18. Actually, depending on the characteristics desired for the transducer calibration, pressure tap 20 may be located anywhere except on the small tube section.

It is therefore apparent that the transducer of the present invention is extremely simple to construct, very compact and yet accurate over a very practical extended range of flow rates.

It is to be understood that the form of this invention as shown in merely a preferred embodiment. Various changes may be made in the function and arrangement of parts; equivalent means may be substituted for those illustrated and described; and certain features may be used independently from others without departing from the spirit and scope of the invention as defined in the following claims.

For instance, laminar flow restrictor 18 need not be located at the end of larger tube 14, so larger tube 14 could continue beyond the location of the laminar flow restrictor.

What is claimed as new and for which Letters Patent of the United States are desired to be secured is:

1. A linear, extended range, flow transducer comprising:
    a first tube section with a gas entry end and a gas exit end;
    a divergent section attached to the gas exit end of the first tube section;
    a single essentially planar laminar flow restrictor of no significant length in the direction of flow attached to the transducer so as to intercept all gas flow through the transducer and located in a plane transverse to the axis of the first tube section and a distance from the internal end of the first tube section which is no greater than two inside diameters of the first tube section; and
    a pressure tap attached to and penetrating a surface of the transducer in a location other than the first tube and located between the laminar flow restrictor and the first tube section.

2. The flow transducer of claim 1 further including a second tube section attached to the end of the divergent section remote from the first tube section, the second tube section being of larger diameter than the first tube section.

3. The flow transducer of claim 2, wherein the laminar flow restrictor is attached to the second tube section.

4. The flow transducer of claim 2 wherein the pressure tap is attached to the second tube section.

5. The transducer of claim 2 wherein the second tube section has an inside diameter in the range of 1 to 4 inches.

6. The transducer of claim 2 wherein the ratio of inside diameters of the second tube section to the first tube section is less than 4 to 1.

7. The transducer of claim 1 wherein the first tube section has an inside diameter in the range of $\frac{1}{2}$ to $1\frac{1}{2}$ inches.

8. The transducer of claim 1 wherein the laminar flow restrictor is a screen.

9. The transducer of claim 1 wherein the laminar flow restrictor is a screen with a mesh in the range of 300 to 800 strands per inch.

10. The transducer of claim 1 wherein the laminar flow restrictor has an open area of at least 15%.

11. The transducer of claim 1 wherein the divergent section has internal surfaces which diverge from the axis of the first tube section at angles in the range of 20 to 90 degrees.

* * * * *